US005658584A

United States Patent [19]

Yamaguchi

[11] Patent Number: 5,658,584
[45] Date of Patent: Aug. 19, 1997

[54] ANTIMICROBIAL COMPOSITIONS WITH HINOKITIOL AND CITRONELLIC ACID

[75] Inventor: Yuzo Yamaguchi, Kanagawa, Japan

[73] Assignee: Takasago International Corporation, Tokyo, Japan

[21] Appl. No.: 513,181

[22] Filed: Aug. 9, 1995

[30] Foreign Application Priority Data

Aug. 19, 1994 [JP] Japan .................................. 6-216686

[51] Int. Cl.$^6$ .......................... A01N 25/00; A01N 25/06; A01N 25/02; A01N 25/08
[52] U.S. Cl. .......................... 424/405; 424/404; 424/408; 424/410; 424/414
[58] Field of Search .................. 424/400, 405, 424/45, 408, 414, 410, 404

[56] References Cited

U.S. PATENT DOCUMENTS

| 4,645,536 | 2/1987 | Butler ................................. 106/15.05 |
| 5,053,222 | 10/1991 | Takasu et al. .................... 514/852 |

FOREIGN PATENT DOCUMENTS

| 1-40005 | 8/1989 | Japan ................................ A61K 7/16 |
| 2-243607 | 9/1990 | Japan ............................. A01N 37/10 |
| 4-182408 | 6/1992 | Japan ............................. A01N 65/00 |
| 5-271073 | 10/1993 | Japan ............................. A61K 31/40 |

OTHER PUBLICATIONS

ROKURO, World Patent Abstract of JP 6048936, Feb. 1994.

Osada et al., Patent Abstracts of Japan, JP 3077801, 1991.

Osamu Okuda, *Koryo Kagaku Soran* (Fragrance Chemistry Comprehensive Bibliography) [II], published by Hirokawa Shoten, (1963) p. 1140.

Yuzo Yamaguchi, *Fragrance Journal*, No. 46, (1981) (Japan) pp. 56–59.

*Primary Examiner*—Edward J. Webman
*Attorney, Agent, or Firm*—Sughrue, Mion, Zinn, Macpeak & Seas

[57] ABSTRACT

An antimicrobial composition containing a mixture of hinokitiol and citronellic acid in a ratio of about 1:1 to about 3:1 by weight. The antimicrobial composition according to the invention is safe for humans and has a high antimicrobial activity and a broad antimicrobial spectrum, and is widely useful for antiblastic and antifungal purposes in toiletries and household articles.

6 Claims, No Drawings

ANTIMICROBIAL COMPOSITIONS WITH HINOKITIOL AND CITRONELLIC ACID

BACKGROUND OF THE INVENTION

1. Field of the Invention

This invention relates to antimicrobial compositions comprising a mixture of hinokitiol and citronellic acid in a specific ratio. The antimicrobial compositions according to the invention are safe for humans, have a high antimicrobial activity and a broad antimicrobial spectrum, and can be widely employed in toiletries and household articles, which need antiblastic or antifungal properties.

2. Description of the Prior Art

Many antimicrobial substances are conventionally known which are chemically synthesized or derived from natural substances. Some of them are officially described in the Official Formulary of Food Additives, The Japanese Standards of Cosmetic Ingredients, etc., and are employed in toiletries and household articles in order to prevent infections by bacteria and fungi. Recently, antimicrobial ingredients in food additives and cosmetic ingredients have been needed for their safety for humans. Therefore, ingredients derived from natural substances are attracting attention because they are said to be very safe.

However, these naturally-occurring antimicrobial substances often have a narrow antimicrobial spectrum, and sometimes are not adequately applicable for toiletries and household articles because they do not meet the requirements of a broad antimicrobial spectrum against various kinds of microorganisms. For example, antimicrobial substances derived from essential oils of spices and herbs have high antimicrobial activity against fungi, but not against bacteria. Antimicrobial substances derived from essential oils of eucalyptus, cinnamon, cedar, sandalwood, etc. are effective against bacteria but not fungi.

Hinokitiol is an effective antimicrobial and is also called β-thujaplicin which is derived from essential oil of *Chamaecyparis taiwanesis* and *Thujopsis dolabrata*, etc., and is known to be one of the compounds having the highest antimicrobial activity and the broadest antimicrobial spectrum among known naturally occurring antimicrobial substances. Hinokitiol has a minimum inhibitory concentration (MIC) of about 1/20000 (50 ppm) against *Eshcerichia coli*, while it has a MIC of about 1/10000 (100 ppm) against Pseudomonas. Hinokitiol is reported to have a low antimicrobial activity against other microorganism as well as Pseudomonas (Yuzo Yamaguchi, *Fragrance Journal*, No. 46 (1981) pp. 56–59).

An antimicrobial agent comprising hinokitiol is disclosed in JP-A-4-182408 (1992) (The term "JP-A" as used herein means an "unexamined published Japanese patent application"). The agent is a fungicide, and is applicable for use on turf, etc., to prevent diseases by inhibiting mold (fungus).

Since hinokitiol has a strong odor, it can be added to toiletries and household articles only in low concentrations so that the effect of the odor is minimized. However, these amounts of hinokitiol are not sufficient to inhibit growth of bacteria belonging to the genus Pseudomonas and mold.

Recently, hinokitiol compositions have been prepared which are combined with other substances to elevate the antimicrobial activity of hinokitiol. For example, JP-A-2-243607 (1990) discloses that a combination of hinokitiol and phenoxyethanol has elevated antimicrobial activity against *Pseudomonas aerginosa*, *Eshcerichia coli*, *Staphylococcus aureus*, *Bacillus subtilis*, *Candida albicans*, and *Aspergillus niger*, which is applicable as antiseptics for toiletries. Also, JP-A-5-271073 (1993) discloses a combination of hinokitiol and indole as an antimicrobial agent which has an elevated antimicrobial activity against *Pseudomonas aeruginosa*.

Citronellic acid is also called 1-rhodinic acid. It is a compound derived from an essential oil of *Chamaecyparis taiwanesis*, etc., and it is known to have an antimicrobial activity against *Fones annosus* and *Mycobacterium tuberculosis* (Osamu Okuda, *Koryo Kagaku Soran* (Fragrance Chemistry Comprehensive Bibliography) [II], 1968. 1.15., issued by Hirokawa Shoten, p. 1140). Also, JP-A-6-40831 (1994) discloses that a plant component derived from Cupressaceae contains β-dolabrin and carvacrol in addition to hinokitiol and 1-rhodinic acid (citronellic acid) and has an antifungal activity against pathogens which cause turf diseases.

JP-B-1-40005 (1989) (The term "JP-B" as used herein means an "examined published Japanese patent application") discloses anti-dental caries compositions comprising hinokitiol and carboxylic acids which have antimicrobial activity against *Streptococcus mutans* causing dental caries. 1-Rhodinic acid (citronellic acid) is described therein as an example of carboxylic acids. However, the antimicrobial activity of compositions comprising hinokitiol and citronellic acid is not definitely described. Although straight chain carboxylic acids such as myristic acid, lauric acid, and oleic acid are described in combination with hinokitiol, the ratio of hinokitiol and carboxylic acid ranges from 1:4 to 1:20 by weight.

As described above, hinokitiol compositions have been described in the art which further include ingredients to increase the antimicrobial activity of hinokitiol. However, several problems are raised: their safety for humans is not guaranteed because the ingredients combined with hinokitiol are not derived from natural substances, use of the compositions is restricted because they provide only a narrow spectrum of activity against microorganisms, etc. Although combinations of hinokitiol and citronellic acid are known, compositions of hinokitiol and citronellic acid in known ratios are not satisfactory because the antimicrobial activity of these compositions is not sufficiently high, they are effective against only a restricted antimicrobial spectrum of microorganisms and their applications are also restricted. Further, no description or suggestion is present in this art on excellent antimicrobial activity of the compositions comprising a specific ratio of the ingredients which has now been found.

SUMMARY OF THE INVENTION

An object of this invention is to provide an antimicrobial composition comprising hinokitiol, which is combined with other safe ingredients, in a specific ratio in order to increase the antimicrobial activity of hinokitiol, in order to provide a broad spectrum of activity against microorganisms including mold and Pseudomonas which are not sufficiently inhibited by hinokitiol only, and in order to use hinokitiol for toiletries and household articles for antiblastic and antifungal purposes.

In order to attain the objects of the present invention, carboxylic acids which are safe for humans were examined, and the antimicrobial activity of compositions comprising hinokitiol and the carboxylic acids was investigated. Citronellic acid among several carboxylic acids was selected, which has been conventionally utilized as a material for medicines and fragrances and has been confirmed to be safe for human beings. As a result, it has been found that a combination of citronellic acid in specific ratios increased the antimicrobial activity of hinokitiol and enlarged the spectrum of antimicrobial effectiveness.

Specifically, the present invention provides an antimicrobial composition comprising hinokitiol and citronellic acid in a ratio ranging from about 1:1 to 3:1 by weight.

DETAILED DESCRIPTION OF PREFERRED EMBODIMENTS

The invention is described in greater detail below.

Hinokitiol utilized in the invention may be derived from conventional sources, for example, from the essential oil of *Chamaecyparis taiwanensis*, *Thujopsis dolabrata*, etc. (hereinafter sometimes described as a "natural product"), by chemical synthesis, and may also be a commercially available article. These hinokitiols are utilized for antiblastic and antifungal purposes of toiletries and household articles. Hinokitiol natural products which are accepted as food additives are preferably utilized for foods.

Hinokitiol salts of sodium, magnesium, copper, calcium, iron, barium, etc., and mixtures thereof may also be utilized for toiletries and household articles.

Citronellic acid utilized in the invention may be a natural product, may be a synthetic product, and may also be a commercially available product. These citronellic acids are utilized for antiblastic and antifungal purposes of toiletries and household articles. Citronellic acid as a natural product is preferably utilized for foods. Since all of (R)-, (S)-, and racemic citronellic acid have been confirmed to have excellent antimicrobial activity when combined with hinokitiol, any citronellic acid isomer and mixtures thereof may be utilized in the invention.

Citronellic acid as a natural product is derived from natural substances as follows; (R)-citronellic acid is extracted from Java citronella oil and geranium oil, (S)-citronellic acid is extracted from pine oil and essential oil of *Chamaecyparis taiwanensis*, and racemic citronellic acid is extracted from camphor oil. Although salts of citronellic acid have been confirmed to have antimicrobial activity, it is significantly less effective than that of free citronellic acid. As a result, free citronellic acid rather than a salt thereof is preferred.

A combination of hinokitiol and citronellic acid in a ratio of about 1:1 by weight is found to have the strongest effect on increasing the antimicrobial activity. When either of the ingredients is present in a larger amount, the antimicrobial effects is reduced. Specifically, use of citronellic acid in a larger mount than that of hinokitiol greatly reduces the antimicrobial effects. When hinokitiol is combined in an amount more than three times the amount of citronellic acid, little synergistic effect is found. Therefore, hinokitiol and citronellic acid are preferably combined in an amount ranging from about 1:1 to 3:1 by weight, more preferably in an amount of about 1:1 by weight according to the invention.

A mixture of hinokitiol and citronellic acid is obtained in a liquid form by directly adding hinokitiol to citronellic acid and stirring the mixture with heating. Although pure hinokitiol is difficult to handle because it is a crystal, the hinokitiol composition according to the invention is prepared in liquid form which is easy to use. A mixture of hinokitiol and citronellic acid in liquid form is more easily prepared by mixing a hinokitiol solution in a non-toxic organic solvent such as ethanol, propylene glycol, and diacetin with citronellic acid, as compared to directly mixing hinokitiol and citronellic acid.

According to the present invention, a mixture of hinokitiol and citronellic acid may be directly added as an antimicrobial composition to foods, toiletries, and household articles for antiblastic and antifungal purposes. Also, the mixture may be prepared in the form of a liquid or as an aerosol by adding non-toxic bases in a suitable amount as needed, and are added or sprayed for antiblastic and antifungal purposes.

Bases added to the mixture are not specifically restricted. Typical, examples of suitable bases are organic solvents such as ethanol, propyleneglycol, glycerin, diacetin and liquefied propellant gas. Antimicrobial compositions according to the invention may also be utilized by soaking sheet substances such as paper, cloth, and non-woven fabrics in the composition.

Antimicrobial compositions according to the invention also may be utilized in combination with other antimicrobial ingredients. By adding antimicrobial compositions according to the invention, the antimicrobial activity of other ingredients can be further enhanced.

Additional ingredients which can be used in combination are not specifically limited as long as they are known antimicrobial substances. Considering safety for human beings, naturally-occurring substances may be preferably utilized. Examples of suitable substances are essential oils such as thyme oil, clove oil, black pepper oil, peppermint oil, mace oil, nutmeg oil, orange oil, sandalwood oil, cedarwood oil, cypress oil, and cinnamon oil, and essential oil ingredients such as phenol derivatives such as thymol, eugenol, carvacrol, dihydroguaiaretic acid, alcohols such as geraniol, citronellol, nerolidole, and farnesol, aldehydes such as citral, citronellal, and cinnamic aldehyde, lactones such as γ-decalactone and δ-decalactone, monoglycerides such as monocaprin and monolaurin, and organic acids such as cinnamic acid, decanoic acid, 3-hydroxydecanoic acid, 9-decenoic acid, and senecionic acid. Of these, the antimicrobial activity of organic acids such as decanoic acid and senecionic acid is greatly elevated by adding such to the composition according to the invention, and these compositions are preferred.

When antimicrobial compositions according to the invention are combined with other antimicrobial ingredients, an amount of the compositions in relation to that of the additional ingredients is preferably about 1:1 to 3:1, more preferably about 1.5:1.

Mixtures of antimicrobial compositions according to the invention and with other antimicrobial ingredients as described above may be directly utilized for antiblastic and antifungal purposes in food, toiletries, and household articles. Mixtures may also be formulated in different preparation forms such as tablets, capsules, powder, granules, liquid preparation, and aerosols by use of known bases. The mixtures may be impregnated into sheet form substances such as paper, cloth, and non-woven fabrics.

The antimicrobial compositions according to the invention have a high antimicrobial activity against a broad spectrum of microorganisms. Examples of microorganisms against which antimicrobial activity is achieved are Gram-positive bacteria such as Bacillus and Staphylococcus, Gram-negative bacteria such as Eshcerichia and Pseudomonas, molds such as Aspergillus, Mucor, and Penicillium, and yeasts such as Candida and Saccharomyces. Specifically, the compositions have a strong antimicrobial activity against molds and bacteria such as *Pseudomonas aeruginosa* which cannot be sufficiently inhibited by hinokitiol only.

Therefore, the antimicrobial compositions according to the present invention may be widely used in foods, toiletries such as lotions, milky lotions, creams, packs, makeup products, hair care products, face washing products, bath products, and anti-sweat preparation, and household articles such as house cleaners, disinfectants, and deodorizers for antiblastic and antifungal purposes.

When the antimicrobial compositions of hinokitiol and citronellic acid according to the invention are added to products for antiblastic and antifungal purposes, the amount of the compositions is preferably from about 0.01 to 0.2% by weight of the total weight of the products. When the antimicrobial compositions according to the invention is sprayed in the air, the mixture of hinokitiol and citronellic acid is preferably sprayed at a level of about 0.1–2 mg/m$^3$. When the antimicrobial compositions according to the invention are impregnated into sheet form in substances, the mixture of hinokitiol and citronellic acid is preferably impregnated at a level of about 0.1–5 mg/m$^2$.

Other ingredients may be added to the products depending on their use. For example, hydrophobic bases such as vaseline, squalane, and bees wax, hydrophilic bases such as propyleneglycol, alcohols such as ethyl alcohol, emulsifying agents such as fatty acid monoglycerides, sorbitan fatty acid esters, and polyoxyethylene alkyl ethers, pigments, and fragrances may be added to a milky lotion. Nutrients, humectants, UV absorber, etc., may be further added to the milky lotion as needed. Products other than a milky lotion may also contain additives suitable for their purposes.

EXAMPLES

The present invention is explained in more detail by referring to the following examples. However, these examples should be regarded as merely illustrative and are not to be construed as limiting the scope of the present invention. Unless otherwise indicated herein, all parts, percents, ratios and the like are by weight.

Example 1

Hinokitiol (manufactured by Takasago International Corporation, hereinafter the same) (10 g) and (R)-citronellic acid (manufactured by Takasago International Corporation, hereinafter the same) (10 g) were dissolved in Japanese Pharmacopeia ethanol to adjust the amount of the resultant solution to 100 ml. An antimicrobial composition was thus prepared which contained hinokitiol and (R)-citronellic acid in an amount of 1:1 by weight.

Example 2

Hinokitiol (10 g) and (S)-citronellic acid (manufactured by Takasago International Corporation, hereinafter the same) (10 g) were dissolved in Japanese Pharmacopeia ethanol to adjust the amount of the resultant solution to 100 ml. An antimicrobial composition was thus prepared which contained hinokitiol and (S)-citronellic acid in an amount of 1:1 by weight.

Example 3

Hinokitiol (15 g) and (S)-citronellic acid (5 g) were dissolved in Japanese Pharmacopeia ethanol to adjust the amount of the resultant solution to 100 ml. An antimicrobial composition was thus prepared which contained hinokitiol and (S)-citronellic acid in an amount of 3:1 by weight.

Experiment 1

The antimicrobial compositions obtained in Examples 1 to 3 were diluted with ethanol 20 times. The diluted solution was utilized as a test solution for the following experiments to evaluate antimicrobial activity against several types of microorganisms.

Brain Heart Infusion medium (manufactured by Nissui Pharm Co., Ltd.) (10 g), dried broth (manufactured by Nissui Pharm Co., Ltd.) (10 g), yeast extract powder (manufactured by Difco Laboratories) (4 g), and agar (14 g) were dissolved in distilled water (1000 ml) by heating, and dispensed in 10 ml portions into test tubes, followed by sterilization under high pressure. After the resultant solutions were heated again to maintain them in solution, the test solution or alcohol without any antimicrobial composition according to the invention (control solution) in an amount of 5–200 µl was added and mixed. Each of the mixtures was poured into a plastic plate (inner diameter: 90 mm) for solidifying.

The solidified plate was divided into 9 fractions. To each fraction, a suspension of test microorganism in distilled water (the number of bacteria or spores: $10^6$ –$10^8$/ml) was inoculated at 5 µl/fraction. After culturing at 30° C. for 48 hours, each fraction was evaluated to determine whether each microorganism grew or not. The minimum inhibitory concentration (MIC, unit: ppm) of each test solution and control solution were determined.

Antimicrobial compositions comprising either hinokitiol or citronellic acid were also prepared and utilized in the same experiment as above in order to elucidate the effect of the combination of hinokitiol and citronellic acid in the antimicrobial composition according to the invention. Comparative compositions comprising hinokitiol and citronellic acid in the following amount were further prepared in the same manner as above for Example 1, and subjected to the same experiment as above in order to determine MIC. The results obtained are shown in Table 1 below.

Comparative Example 1 hinokitiol: (S)-citronellic acid=4:1 (weight ratio)

Comparative Example 2 hinokitiol: (S)-citronellic acid=1:3 (weight ratio)

Comparative Example 3 hinokitiol: (S)-citronellic acid=1:4 (weight ratio)

The microorganisms utilized in Experiment 1 were as follows.

Gram-positive bacteria; Bs: *Bacillus subtilis* IFO3009

Sa: *Staphylococcus aureus* IAM1011

Gram-negative bacteria; Ec: *Eshcerichia coli* AHU1410

Pa: *Pseudomonas aeruginosa* IFO13275

Mold (fungus); An: *Asperigillus niger* IAM2534

Mj: *Mucor jansenii* AHU6009

Pf: *Penicillium frequentans* AHU8286

Yeast; Ct: *Candida tropicalis* AHU3410

Sc: *Saccharomyces cerevisiae* IFO2030

TABLE 1

| Test Solutions | Bs | Sa | Ec | Pa | An | Mj | Pf | Ct | Sc |
|---|---|---|---|---|---|---|---|---|---|
| Hinokitiol [H] | 50 | 50 | 50 | 100 | 100 | 100 | 100 | 50 | 50 |
| (R)-citronellic acid [R] | 500 | 500 | 500 | >1000 | 1000 | 1000 | 1000 | 1000 | 500 |
| (S)-citronellic acid [S] | 500 | 500 | 500 | >1000 | 1000 | 1000 | 1000 | 1000 | 500 |
| Example 1 (H:R = 1:1) | 40 | 40 | 40 | 40 | 40 | 32 | 40 | 40 | 20 |
| Example 2 (H:S = 1:1) | 40 | 40 | 40 | 40 | 40 | 32 | 40 | 40 | 20 |
| Example 3 (H:S = 3:1) | 40 | 50 | 40 | 60 | 40 | 40 | 40 | 50 | 40 |
| Comparative Example 1 (H:S = 4:1) | 50 | 50 | 50 | 100 | 100 | 100 | 100 | 50 | 50 |
| Comparative Example 2 (H:S = 1:3) | 250 | 250 | 500 | 1000 | 500 | 500 | 500 | 250 | 250 |
| Comparative Example 3 (H:S = 1:4) | 500 | 500 | 500 | 1000 | 1000 | 500 | 1000 | 1000 | 500 |

As shown in the Table 1 above, the MIC against Bs is 50 ppm for hinokitiol only and is 500 ppm for either (R)- or (S)-citronellic acid, while the MIC is reduced to a total amount of 40 ppm for the combination of hinokitiol and (R)- or (S)-citronellic acid (at a ratio of hinokitiol and (R)- or (S)-citronellic acid of 20 ppm: 20 ppm or 30 ppm: 10 ppm).

It is apparent from the results in Table 1 above that hinokitiol at even lower concentrations has an excellent antimicrobial activity, i.e., the activity of hinokitiol is elevated in combination with citronellic acid.

Antimicrobial activity against microorganisms other than Bs was found to be elevated by combining hinokitiol and citronellic acid. Specifically, the antimicrobial activity is remarkably elevated against Pa, An, Mj, and Pf which are not sufficiently inhibited by hinokitiol only, and the antimicrobial spectrum of hinokitiol is enlarged on combination with citronellic acid.

Experiment 2

Compositions comprising hinokitiol and one of two carboxylic acids other than citronellic acid were prepared by combining the substances in an amount of 1:1 by weight in the same manner as above in Example 1, and diluted with ethanol 20 times. The resultant test solutions (Comparative Examples 4 and 5) were subjected to the same experiment as Experiment 1 in order to determine the MIC (unit: ppm) against several kinds of microorganisms. The MIC of each carboxylic acid alone was also determined. The results obtained are shown in Table 2 below.

The microorganisms utilized in Experiment 2 were as follows.

Gram-positive bacteria; Bs: *Bacillus subtilis var niger* IFO3108

Gram-negative bacteria; Pa: *Pseudomonsa aerginosa* IAM1202

Mold (fungus); An: *Aspergillus niger* AHU7217

Yeast; Sc: *Saccharomyces cerevisiae* AHU3028

As described above, a microorganism of the same species but different strains than used in Experiment 1 was utilized. Therefore, some MIC values for hinokitiol are different from those in Experiment 1.

TABLE 2

| Test Solutions | Bs | Pa | An | Sc |
|---|---|---|---|---|
| Hinokitiol [H] | 50 | 50 | 50 | 50 |
| Decanoic acid [D] | 500 | >1000 | 500 | >1000 |
| Myristic acid [M] | 2000 | >2000 | 2000 | 1000 |
| Comparative Example 4 (H:D = 1:1) | 130 | 250 | 130 | 100 |
| Comparative Example 5 (H:M = 1:1) | 130 | 250 | 130 | 100 |

As shown by the results in Table 2 above, MIC against *Saccharomyces cerevisiae* (Sc) is 50 ppm for hinokitiol only and 1000 ppm or more for decanoic acid, while the total MIC of the composition of hinokitiol and decanoic acid is 100 ppm (concentration of hinokitiol and decanoic acid: 50 ppm and 50 ppm). It is apparent that the MIC of hinokitiol is not changed and the antimicrobial activity of hinokitiol is not elevated at all even in combination with decanoic acid.

Similarly, the antimicrobial activity of hinokitiol is not elevated at all against microorganisms other than Sc even in combination with decanoic acid or myristic acid.

Example 4

According to the following formulation, ingredients (a) were heated to 75° C. and ingredients (b) were heated to 73° C. for dissolution. Next, ingredients (a) were added to ingredients (b) with stirring for emulsification. To the emulsion, the antimicrobial composition obtained in Example 1 and fragrance were added and uniformly mixed to prepare 100 g of a milky lotion.

TABLE 3

| Ingredients | Contents (weight %) |
|---|---|
| Antimicrobial composition obtained Example 1 | 0.2 |
| ingredients (a): | |
| squalane | 5.0 |
| vaseline | 2.0 |
| bleached bees wax | 0.5 |
| sorbitan sesquioleate | 0.8 |
| polyoxyethylene oleyl ether (20 E.O.) | 1.2 |
| ingredients (b): | |
| 2% xanthan gum solution | 20.0 |
| propyleneglycol | 5.0 |
| ethyl alcohol | 4.0 |
| purified water | 61.1 |
| fragrance | 0.2 |

Example 5

Shampoo composition

Ingredients of the following formulation were mixed to prepare a shampoo composition (100 g).

TABLE 4

| Ingredients | Contents (weight %) |
|---|---|
| Antimicrobial composition obtained in Example 2 | 0.25 |
| decanoic acid | 0.05 |
| lauryl sulfate triethanolamine | 18.0 |
| hydroxypropylmethylcellulose | 15.0 |
| lauryl sulfate ammonium | 8.0 |
| cocamide | 4.0 |

TABLE 4-continued

| Ingredients | Contents (weight %) |
| --- | --- |
| palmitic acid | 0.3 |
| 1,3-dimethylol-5,5-dimethylhydantoin | 0.15 |
| sodium ethylenediamine tetraacetate | 0.05 |
| citric acid | a small amount |
| salt | a small amount |
| fragrance | 0.85 |
| water | a residual amount |

Example 6

Disinfectant

Ingredients of the following formulation were uniformly mixed to prepare a disinfectant (100 g).

TABLE 5

| Ingredients | Contents (weight %) |
| --- | --- |
| Antimicrobial composition obtained in Example 3 | 0.5 |
| decanoic acid | 0.1 |
| ethanol | 1.8 |
| isopropyl alcohol | 0.9 |
| xylenol | 1.5 |
| fragrance | 1.0 |
| soap | 15.0 |
| water | 79.2 |

Example 7

Detergent

Ingredients of the following formulation were uniformly mixed to prepare a detergent (100 g).

TABLE 6

| Ingredients | Contents (weight %) |
| --- | --- |
| Antimicrobial composition obtained in Example 1 | 0.5 |
| senecionic acid | 0.1 |

TABLE 6-continued

| Ingredients | Contents (weight %) |
| --- | --- |
| white soft paraffine | 6.0 |
| alkylallyl sulfonate polymer | 50.0 |
| cholesterol | 2.0 |
| water | 41.4 |

According to the present invention, antimicrobial compositions which are safe for humans and which have a high antimicrobial activity and a broad antimicrobial spectrum can be prepared by combining a mixture comprising hinokitiol and citronellic acid in amounts of 1:1–3:1 by weight. The compositions are useful for toiletries and household articles for antiblastic and antifungal purposes.

While the invention has been described in detail and with reference to specific embodiments thereof, it will be apparent to one skilled in the art that various changes and modifications can be made therein without departing from the spirit and scope thereof.

What is claimed is:

1. A method of inhibiting bacterial and yeast growth comprising applying to a subject a composition comprising hinokitiol and citronellic acid as active ingredients in a ratio ranging from about 1:1 to about 3:1 by weight.

2. The method of claim 1, wherein said bacterial growth is *Pseudomonas aerginosa*.

3. A method of inhibiting the growth of a microorganism selected from the group consisting of Aspergillus, Mucor and Penicillium comprising applying to a subject a composition comprising hinokitiol and citronellic acid as active ingredients in a ratio ranging from about 1:1 to about 3:1 by weight.

4. The method of claim 3, wherein said Aspergillus is *Aspergillus niger*.

5. The method of claim 3, wherein said Mucor is *Mucor jansenii*.

6. The method of claim 3, wherein said Penicillium is *Penicillium frequentars*.

\* \* \* \* \*